United States Patent [19]

Lacroix et al.

[11] Patent Number: 5,260,480
[45] Date of Patent: Nov. 9, 1993

[54] QUATERNIZATION PROCESS

[75] Inventors: Christian Lacroix; Raymond Hess, both of Forbach, France

[73] Assignee: Norsolor, France

[21] Appl. No.: 883,930

[22] PCT Filed: Feb. 2, 1989

[86] PCT No.: PCT/FR89/00036
§ 371 Date: Sep. 7, 1990
§ 102(e) Date: Sep. 7, 1990

[87] PCT Pub. No.: WO89/07588
PCT Pub. Date: Aug. 24, 1989

Related U.S. Application Data

[63] Continuation of Ser. No. 754,317, Sep. 4, 1991, abandoned, which is a continuation of Ser. No. 543,716, Sep. 7, 1990, abandoned.

[30] Foreign Application Priority Data

Feb. 11, 1988 [FR] France ............... 88/01635

[51] Int. Cl.⁵ ............................................. C07C 69/52

[52] U.S. Cl. .................................... 560/222; 564/204; 564/207

[58] Field of Search ................. 560/222; 564/204, 207

[56] References Cited

U.S. PATENT DOCUMENTS 4,745,214 5/1988 Hess et al. ............................ 560/222

FOREIGN PATENT DOCUMENTS 0250325 12/1987 European Pat. Off. .

Primary Examiner—Paul J. Killos
Attorney, Agent, or Firm—Finnegan, Henderson, Farabow, Garrett & Dunner

[57] ABSTRACT

A process for the preparation of aqueous solutions of unsaturated quaternary ammonium salts corresponding to the following formula:

$$H_2C=C(R_3)-C(O)-A-R_4-N^+(R_1)(R_2)(R)X^-$$

9 Claims, No Drawings

QUATERNIZATION PROCESS

This application is a continuation of application Ser. No. 07/754,317, filed Sep. 4, 1991, now abandoned, which is a continuation of Ser. No. 07/543,716, filed Sep. 7, 1990, abandoned.

The present invention relates o a process for the preparation of aqueous solutions of unsaturated quaternary ammonium salts corresponding to the following formula (I):

$$H_2C=C(R_3)-C(O)-A-R_4-N^+(R_1)(R_2)(R)X^-$$

in which:
A is an oxygen atom or an NH group,
$R_3$ is a hydrogen atom or a methyl radical,
$R_4$ is a linear or branched alkyl radical with 1 to 6 carbon atoms,
$R_1$, $R_2$ and R, which are different or identical, are an alkyl radical or an aryl radical,
X is chosen from Cl, Br, I, $CH_3$-$CO_3$ or $CH_3$-$SO_4$.

There is a known process, described in European Application 250,325, for the preparation of aqueous solutions of unsaturated quaternary ammonium salts (I) according to which, in the presence of at least one polymerization inhibitor:

in a first stage (a) at least one (meth)acrylic monomer (II) of formula $H_2C=C(R_3)-C(O)-A-R_4-N(R_1)(R_2)$ (in which $R_1$, $R_2$, $R_3$, $R_4$ and A have the meaning referred to above) is reacted with 5 to 20% by weight of the quantity necessary for the reaction of a quaternising agent (III) of formula RX (with R and X having the abovementioned meaning), or, instead of RX, with 5 to 20% by weight of an aqueous solution of unsaturated quaternary ammonium salts (I) (given in relation to the weight of (meth)acrylic monomers (II)), this solution comprising 50 to 85% by weight of quaternary ammonium salts (I), in a second stage (b) water and the quaternising agent (III) are added continuously until the desired concentration of unsaturated quaternary ammonium salts is obtained in the water.

During the stages (a) and (b), the temperature is maintained between 30° and 60° C. Furthermore, during the stages (a) and (b) and in particular as the end of the reaction approaches, a stream of oxygen-containing gas is maintained in the reaction mixture, such that the volume ratio (or volumetric flow rate) of total gas at the exit of the reactor to the volume (or volumetric flow rate) of oxygen introduced at the entry of the same reactor is lower than 100.

The process according to European Application 250,325 makes it possible to prepare aqueous solutions of unsaturated quaternary ammonium salts (I) which have a room temperature stability of more than a year. However, the presence of impurities is found in these solutions, in particular of $CH_2=C(R_3)-C(O)-A-R$-(IV), $CH_2=C(R_3)-C(O)-AH$ (V) and of (meth)acrylic monomers (II). The content of these impurities is particularly high when $R_3$ is a hydrogen atom and when A denotes an oxygen atom; it can then be up to values of 3000–5000 ppm, 0.69% and 1.3% by weight respectively in the case of the impurities. (IV), (V) and (II).

The Applicant Company has found a process for the preparation of aqueous solutions of unsaturated quaternary ammonium salts (I) enabling the formation of the impurities to be considerably reduced during the quaternization reaction, this process also having the advantage of yielding solutions whose room temperature stability exceeds a year.

More precisely, the subject of the present invention is a process for the preparation of aqueous solutions of unsaturated quaternary ammonium salts (I) corresponding to the following formula:

$$H_2C=C(R_3)-C(O)-A-R_4-N^+(R_1)(R_2)(R)X^-$$

from at least one (meth)acrylic monomer (II) of formula $H_2C=C(R_3)-C(O)-A-R_4-N(R_1)(R_2)$ and from at least one quaternizing agent (III) of formula RX, in which formulae R, $R_1$, $R_2$, $R_3$, $R_4$, A and X have the abovementioned meaning, in the presence of at least one polymerization inhibitor, in which process the reaction is carried out at a temperature of between 10° C. and 80° C., and in which (a) in a first stage, all or a part of the quaternizing agent (III) necessary for the reaction is introduced into the reactor, this agent (III) being in the liquid state in the reaction conditions, (b) then, at least one (meth)acrylic monomer (II) is added, and (c) as soon as 0 to 30% of the stoichiometry of the (meth)acrylic monomer(s) has been introduced into the reactor, the remainder of the quaternizing agent (III), the remainder of (meth)acrylic monomers and the water are added continuously and simultaneously until the desired concentration of unsaturated quaternary ammonium salts (I) has obtained, (d) and, in the case where the quaternizing agent (III) is in the gaseous state at the reaction temperature, the reaction is carried out in the presence of oxygen and a pressure is applied in order that the quaternizing agent should be in the liquid state at the reaction temperature and, at the end of reaction, the pressure is gradually reduced to atmospheric pressure and simultaneously a ratio of volumetric flow rate of total gas at the exit of the reactor to the volumetric flow rate of oxygen introduced into the reactor which is lower than 100, and preferably lower than 50, is applied.

During the reaction, the temperature is preferably kept between 30° and 60° C.

During stage (c), the flow rate of water, of the (meth)acrylic monomers (II) and optionally of quaternising agent (II) are preferably controlled so as to maintain in the reaction mixture a solution which is saturated or close to saturation with unsaturated quaternary ammonium salts (I).

The introduction of the remainder of quaternizing agent (III), of the remainder of (meth)acrylic monomers (II) and of water in stage (c) is preferably carried out as soon as 10 to 20% of the stoichiometry of the (meth)acrylic monomer(s) has been introduced into the reactor in accordance with stage (b).

In the case where the quaternizing agent is in the liquid state at the reaction temperature, the reaction can be carried out in the presence of oxygen under reduced pressure or under pressure. Preferably, however, in this precise case atmospheric pressure is applied and the reaction is optionally carried out in the presence of oxygen.

As soon as the reaction is finished, the traces of volatile quaternizing agents (III) dissolved in the reaction mixture are removed by purging the mixture, under reduced pressure or at atmospheric pressure, with the aid of an oxygen-containing gas such as air or pure oxygen.

The process according to the invention is suitable especially for the preparation of aqueous solutions containing mixtures of unsaturated quaternary ammonium salts (I) (called mixed salt solutions hereinafter). If the quaternizing agents (III) necessary for preparing these mixed salt solutions are, in the case of some, gaseous at the reaction temperature and, in the case of others, liquid at the reaction temperature, it is recommended to introduce firstly the liquid quaternizing agents (III) and only then the gaseous quaternizing agents (III). The procedure is then preferably as follows:

the reaction is carried out in the presence of at least one polymerization inhibitor between at least one (meth)-acrylic monomer (II) and at least one quaternizing agent (III) and is distinguished in that it is carried out at a temperature of between 10° C. and 80° C., and preferably between 30° and 60° C., in that, ($a_1$) in a first stage, all or a part of the liquid quaternising agent(s) (III) is introduced into the reactor, ($b_1$) then, at least one (meth)acrylic monomer (II) is added, and ($c_1$) as soon as 0 to 30% of the stoichiometry of the (meth)acrylic monomer(s) has been introduced into the reactor, the remainder of quaternizing agent (III) which is liquid at the reaction temperature, all or a part of the remainder of the (meth)acrylic monomers (II) necessary for the reaction and all or a part of the water necessary for the reaction are added continuously and simultaneously, the total quantity of said quaternising agent (III) which is liquid at the reaction temperature representing 0.1% to 99.9% of the stoichiometry in relation to said (meth)acrylic monomers (II), ($d_1$) and then, the quaternizing agent(s) (III) gaseous at the reaction temperature, the remainder of the (meth)-acrylic monomers (II) and the remainder of water are added continuously and simultaneously until the desired concentration of unsaturated quaternary ammonium salts (I) is obtained, the sum of the quantities of quaternizing agents added in stages ($a_1$), ($c_1$) and ($d_1$) corresponding to a value equal to or higher than the stoichiometry in relation to the (meth)acrylic monomers (II), the reaction being then carried out in the presence of oxygen at atmospheric pressure or at a higher pressure, and in that, during the reaction, at the end of reaction and during the application of atmospheric pressure a ratio of volumetric flow rate of total gas at the exit of the reactor to the volumetric flow rate of oxygen introduced into the reactor which is lower than 100, and preferably lower than 50, is applied.

Stage ($a_1$) can be carried out under pressure or at a reduced pressure. It is preferably carried out at atmospheric pressure.

The process according to the invention is suitable for the quaternization of (meth)acrylic monomers (II) capable of being hydrolyzed, such as dimethylaminoethyl acrylate dimethylaminopropyl acrylate and the corresponding methacrylates, and for dimethylaminopropylacrylamide and for dimethylaminopropylmethacrylamide.

The quaternizing agents (III) which are suitable for the present invention are especially halogenated hydrocarbons. Among the quaternizing agents (III) which are liquid under normal temperature and pressure conditions there may be mentioned methyl iodide, ethyl bromide, ethyl iodide and benzyl chloride; dimethyl sulfate and dimethyl carbonate are also suitable. Among the quaternizing agents (III) which are gaseous under normal temperature and pressure conditions there may be mentioned methyl chloride, methyl bromide and ethyl chloride.

Among the polymerization inhibitors which are suitable for the process according to the invention there may be mentioned 3,5-di-tert-butyl-4-hydroxy toluene, hydroquinone methyl ether, phenothiazine, hydroquinone, catechol and tert-butyl-catechol. From 100 ppm to 5000 ppm of polymerization inhibitor is preferably employed relative to the (meth)acrylic monomer (II).

The process according to the invention makes it possible to prepare aqueous solutions of unsaturated quaternary ammonium salts (I) which have concentrations of the order of 50 to 85% by weight of salts (I) in water. In addition, these aqueous solutions contain very low quantities of impurities which do not exceed 200 ppm of $CH_2=C(R_3)-C(O)-A-R$, 0.4% by weight of $CH_2=C(R_3)-C(O)-AH$ and 0.5% by weight of (meth)acrylic monomers (II) (with R, $R_3$ and A having the meaning given above).

The examples which follow and which are given by way of guidance, will allow the invention to be understood better. In these examples the percentages are expressed in % by weight.

EXAMPLE 1 (COMPARATIVE)

Preparation Of An Aqueous Solution Containing 80% Of Acryloyloxyethyltrimethylammonium Chloride 515 g of dimethylaminoethyl acrylate stabilized with the aid of 700 ppm of hydroquinone methyl ether are charged with stirring into a jacketed reactor. Throughout the reaction period, 0.2 Nl/h of air is injected continuously into the reactor and the following are maintained:

the temperature at 47° C.

atmospheric pressure the blow-off exit flow rate lower than 0.7 Nl/h (that is a ratio of the volumetric flow rates of the blow-off to the oxygen introduced into the reactor lower than 17.5).

In the first stage, 18 g of methyl chloride ($CH_3Cl$) are injected into the reactor at a flow rate of 30 g/h (that is 11% of the total quantity of $CH_3Cl$ needed for the reaction) and then, in a second stage, methyl chloride and water are injected simultaneously and continuously in a water/$CH_3Cl$ weight ratio of between 0.9 and 1.0 (whence a water/$CH_3Cl$ molar ratio of between 2.5 and 2.8). As the end of the reaction approaches, the flow rate of methyl chloride is progressively reduced to 10 g/h and the blow-off exit flow rate is kept lower than 1 Nl/h (whence a ratio of the volumetric flow rates of the blow-off to the oxygen at the reactor entry lower than 25). The operation is stopped after 8 hours' reaction. 174 g of water and 196 g of methyl chloride have been employed in this operation and 865 g of acryloyloxyethyltrimethylammonium chloride at a concentration of 80% in water are recovered. The final product is then subjected to an injection of air at a flow rate of 7 Nl/h for ½ hour hot and then for ½ hour at room temperature. The final product obtained has the following characteristics: water: 20.4% acrylic acid: 0.69% dimethylaminoethyl acrylate: 1.3% methyl chloride: 15 ppm polymer: nil storage stability: longer than 1 year.

EXAMPLE 2

Preparation Of An Aqueous Solution Containing 80% Of Acryloyloxyethyltrimethylammonium Chloride 78 g of liquid methyl chloride are charged with stirring into a jacketed reactor. The temperature is raised to 47° C. and the pressure of the system equilibrates at 9.6 bars absolute. In the first stage 33 g of dimethylaminoethyl acrylate stabilized with the aid of 700 ppm of hydroquinone methyl ether are injected into the reactor over a period of 20 minutes (that is 16% of the total quantity of acrylate necessary for reaction) In a second stage the complement of the acrylate and the water are injected simultaneously and continuously in a water/acrylate weight ratio of the order of 0.4 over a period of 2 hours. Throughout the reaction the temperature is kept at 47° C. and the pressure in the reactor drops to 3.2 bars absolute at the end of the injection of reactants. 0.5 Nl/h of air is then injected continuously into the reactor and over a period of 1 hour the reactor pressure is returned progressively to atmospheric pressure while a blow-off exit flow rate lower than 1.5 Nl/h is maintained (whence a ratio of the blow-off volumetric flow rates to the oxygen introduced lower than 15). 71 g of water and 205 g of dimethylaminoethyl acrylate have been employed in this operation and 343 g of acryloyloxyethyltrimethylammonium at a concentration of. 80% in water are recovered. The final product is then subjected to an injection of air at a flow rate of 7 Nl/h for ½ hour hot and then for ½ hour at room temperature. The final product obtained has the following characteristics: water: 20.3% acrylic acid: 0.23% dimethylaminoethyl acrylate: 0.15% methyl chloride: 10 ppm polymer: nil storage stability: longer than 1 year.

EXAMPLE 3 (COMPARATIVE)

Preparation Of An Aqueous Solution Containing 80% Of Acryloyloxyethylbenzyldimethylammonium Chloride 429 g of dimethylaminoethyl acrylate stabilized with the aid of 700 ppm of hydroquinone ether are charged with stirring into a jacketed reactor. Throughout the reaction period, that is 4 hours in all, the temperature is kept at 50° C. and the air at a continuous flow rate of 0.2 Nl/h. Benzyl chloride is introduced into the reactor at a flow rate of 80 g/h for 45 minutes, that is 15.8% of the total quantity of chloride necessary for the reaction. The complement of benzyl chloride and the water are then introduced simultaneously and continuously at flow rates of 110 g/h and 65 g/h respectively. 202 g of water and 380 g of benzyl chloride have been employed in this operation and 1010 g of acryloyloxyethylbenzyldimethylammonium chloride at a concentration of 80% in water are recovered. The final product obtained has the following characteristics: water: 20.1% acrylic acid: 0.50% dimethylaminoethyl acrylate: 0.60% benzyl acrylate: 2200 ppm polymer: nil storage stability: longer than 1 year.

EXAMPLE 4

Preparation Of An Aqueous Solution Containing 80% Of Acryloyloxyethylbenzyldimethylammonium Chloride 380 g of benzyl chloride are charged with stirring into a jacketed reactor. Throughout the reaction period, that is 4 hours in all, the temperature is kept at 50° C. and the air at a continuous flow rate of 0.2 Nl/h. Dimethylaminoethyl acrylate (stabilized with the aid of 700 ppm of hydroquinone methyl ether) is introduced into the reactor at a flow rate of 100 g/h for 45 minutes, that is 17.5% of the total quantity of acrylate necessary for the reaction. The complement of dimethylaminoethyl acrylate and the water are then introduced simultaneously and continuously at flow rates of 120 g/h and 65 g/h respectively. 202 g of water and 429 g of dimethylaminoethyl acrylate have been employed in this operation and 1010 g of acryloyloxyethylbenzyldimethylammonium chloride at a concentration of 80% in water are recovered. The final product obtained has the following characteristics: water: 20.1% acrylic acid: 0.25% dimethylaminoethyl acrylate: 0.21% benzyl acrylate: 200 ppm polymer: nil storage stability: longer than 1 year.

EXAMPLE 5

Preparation Of An Aqueous Solution Containing 80% Of A Mixture Of Acryloyloxyethylbenzyldimethylammoniun Chloride And Of Acryloyloxyethyltrimethylammonium Chloride 360 g of benzyl chloride are charged with stirring into a jacketed reactor. Throughout the reaction period, that is 5 hours in all, the temperature is kept at 50° C. and the air at a continuous flow rate of 0.2 Nl/h. Dimethylaminoethyl acrylate (stabilized with the aid of 700 ppm of hydroquinone methyl ether) is introduced into the reactor at a flow rate of 100 g/h for 45 minutes, that is 17.5% of the total quantity of acrylate necessary for the reaction. The complement of dimethylaminoethyl acrylate and the water are then introduced simultaneously and continuously at flow rates of 120 g/h and 60 g/h respectively. After 3.5 hours' reaction, methyl chloride is injected into the reactor at a flow rate of 15 g/h for 1.5 hours while the blow-off exit flow rate is kept lower than 1 Nl/h (whence a ratio of blow-off volumetric flow rates to the oxygen introduced lower than 25). 200 g of water, 429 g of dimethylaminoethyl acrylate and 22.5 g of methyl chloride were employed in all in this operation. 997 g of aqueous solution of a mixture of 2 quaternary ammonium salts at a concentration of 80% in water are recovered. The final product is then subjected to an injection of air at a flow rate of 7 Nl/h for ½ hour hot and ½ hour at room temperature. The final product obtained has the following characteristics: water: 20.2% acrylic acid: 0.29% dimethylaminoethyl acrylate: 0.28% benzyl acrylate: 150 ppm benzyl chloride: 10 ppm methyl chloride: 10 ppm polymer: nil storage stability: longer than 1 year.

What is claimed is:

1. A process for the preparation of aqueous solutions of unsaturated quaternary ammonium salts corresponding to the following formula (I):

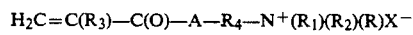

in which:

A is an oxygen atom or an NH group, $R_3$ is a hydrogen atom or a methyl radical, $R_4$ is a linear or branched alkyl radical with 1 to 6 carbon atoms, $R_1$, $R_2$ and R, which are different or identical, are an alkyl radical or an aryl radical, X is chosen from Cl, Br, I, $CH_3$-$CO_3$ or $CH_3$-$SO_4$, from at least one (meth)acrylic monomer (II) of formula $H_2C=C(R_3)—C(O)—A—R_4—N(R_1)(R_2)$ and from at least one quaternizing agent (III) of formula RX, in which formulae R, $R_1$, $R_2$, $R_3$, $R_4$, A and X have the above-mentioned meaning, in the presence of at least one polymerization inhibitor, in which process the reaction is carried out at a temperature of between 10° C. and 80° C., and in which (a) in a first stage, all or a part of the quaternizing agent (III) necessary for the is introduced into the reactor, this agent (III) being in the liquid state in the reaction conditions, (b) then, at least one (meth)acrylic monomer (II) is added, and (c) as soon as 0 to 30% of the stoichiometry of the (meth)acrylic monomer(s) has been introduced into the reactor, the remainder of quaternizing agent (III), the remainder of (meth)acrylic monomers and the water are added continuously and simultaneously until the desired concentration of unsaturated quaternary ammonium salts (I) has been obtained, (d) and, in the case where the quaternizing agent (III) is in the gaseous state at the reaction temperature, the reaction is carried out in the presence of oxygen and a pressure is applied in order that the quaternizing agent should be in the liquid state and, at the end of reaction, the pressure is gradually decreased to atmospheric pressure and simultaneously a ratio of volumetric flow rate of total gas at the exit of the reactor to the volumetric flow rate of oxygen introduced into the reactor which is lower than 100 is applied.

2. The process as claimed in claim 1, wherein, in the case (d) a ratio of volumetric flow rate of total gas at the exit of the reactor to the volumetric flow rate of oxygen introduced into the reactor which is lower than 50 is applied.

3. The process as claimed in claim 1, wherein the temperature is kept between 30° and 60° C. during the reaction.

4. The process as claimed in claim 1, wherein the introduction of the remainder of quaternizing agent (III), of the remainder of (meth)acrylic monomers (II) and of water in stage (c) is carried out as soon as 10 to 20% of the stoichiometry of the (meth)acrylic monomer(s) has been introduced in accordance with stage (b).

5. The process as claimed in claim 1, wherein the reaction is carried out at a temperature of between 10 and 80° C. wherein, ($a_1$) in a first stage, all or a part of the liquid quaternizing agent(s) (III) is introduced into the reactor, ($b_1$) then, at least one (meth)acrylic monomer (II) is added, and (c) as soon as 0 to 30% of the stoichiometry of the (meth)acrylic monomer(s) has been introduced into the reactor, the remainder of quaternizing agent (III) which is liquid at the reaction temperature, all or a part of the remainder of the methacrylic monomers (II) necessary for the reaction and all or a part of the water necessary for the reaction are added continuously and simultaneously, the total quantity of said quaternizing agent (III) which is liquid at the reaction temperature representing 0.1% to 99.9% of the stoichiometry in relation to said (meth)acrylic monomers (II), ($d_1$) and then, the quaternizing agent(s) (III) gaseous at the reaction temperature, the remainder of the (meth)acrylic monomers (II) and the remainder of water are added continuously and simultaneously until the desired concentration of unsaturated quaternary ammonium salts (I) is obtained, the sum of the quantities of quaternizing agents added in stages ($a_1$), ($c_1$) and ($d_1$) corresponding to a value equal to or higher than the stoichiometry in relation to the (meth)acrylic monomers (II), the reaction being then carried out in the presence of oxygen at atmospheric pressure or at a higher pressure, and wherein, during the reaction, at the end of reaction and during the application of atmospheric pressure a ratio of volumetric flow rate of total gas at the exit of the reactor to the volumetric flow rate of oxygen introduced into the reactor which is lower than 100 is applied.

6. The process as claimed in claim 2, wherein the temperature is kept between 30° and 60° C. during the reaction.

7. The process as claimed in claim 2, wherein the introduction of the remainder of quaternizing agent (III), of the remainder of (meth)acrylic monomers (II) and of water in stage (c) is carried out as soon as 10 to 20% of the stoichiometry of the (meth)acrylic monomer(s) has been introduced in accordance with stage (b).

8. The process as claimed in claim 3, wherein the introduction of the remainder of quaternizing agent (III), of the remainder of (meth)acrylic monomers (II) and of water in stage (c) is carried out as soon as 10 to 20% of the stoichiometry of the (meth)acrylic monomer(s) has been introduced in accordance with stage (b).

9. The process as claimed in claim 6, wherein the introduction of the remainder of quaternizing agent (III), of the remainder of (meth)acrylic monomers (II) and of water in stage (c) is carried out as soon as 10 to 20% of the stoichiometry of the (meth)acrylic monomer(s) has been introduced in accordance with stage (b).

* * * * *

UNITED STATES PATENT AND TRADEMARK OFFICE
CERTIFICATE OF CORRECTION

PATENT NO. : 5,260,480

DATED : November 9, 1993

INVENTOR(S) : Christian Lacroix et al

It is certified that error appears in the above-indentified patent and that said Letters Patent is hereby corrected as shown below:

In claim 1, col. 6, line 57, formula (I) should read $$H_2C=C(R_3)-C(O)-A-R_4-N^+(R_1)(R_2)(R).X^-$$

col. 7, line 9, after "for the" and before "is" insert

UNITED STATES PATENT AND TRADEMARK OFFICE
CERTIFICATE OF CORRECTION

PATENT NO. : 5,260,480
DATED : November 9, 1993
INVENTOR(S) : Christian Lacroix et al It is certified that error appears in the above-indentified patent and that said Letters Patent is hereby corrected as shown below:

After claim 9, insert claims 10-12:

—10. The process as claimed in claim 5, wherein the reaction is carried out at a temperature of between 30 and 60°C.

11. The process as claimed in claim 5, wherein the ratio of volumetric flow rate of total gas at the exit of the reactor to the volumetric flow rate of oxygen introduced into the reactor in stage ($d_1$) is lower than 50

12. The process as claimed in claim 5, wherein the reaction is carried out at a temperature of between 30 and 60°C and the ratio of volumetric flow rate of total gas at the exit of the reactor to the volumetric flow rate of oxygen introduced into the reactor in stage ($d_1$) is lower than 50

Signed and Sealed this

Third Day of May, 1994

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,260,480

DATED : November 9, 1993

INVENTOR(S) : Christian Lacroix et al.

It is certified that error appears in the above-identified patent and that said Letters Patent is hereby corrected as shown below:

In claim 1, col. 6, line 57, formula (I) should read $$H_2C=C(R_3)-C(O)-A-R_4-N^+(R_1)(R_2)(R).X^-$$

col. 7, line 9, after "for the" and before "is" insert --reaction--.

After claim 9, insert claims 10-12:

--10. The process as claimed in claim 5, wherein the reaction is carried out at a temperature of between 30 and 60°C.

11. The process as claimed in claim 5, wherein the ratio of volumetric flow rate of total gas at the exit of the reactor to the volumetric flow rate of oxygen introduced into the reactor in stage ($d_1$) is lower than 50.

UNITED STATES PATENT AND TRADEMARK OFFICE
CERTIFICATE OF CORRECTION

PATENT NO. : 5,260,480
DATED : November 9, 1993
INVENTOR(S) : Christian Lacroix et al.

It is certified that error appears in the above-identified patent and that said Letters Patent is hereby corrected as shown below:

12. The process as claimed in claim 5, wherein the reaction is carried out at a temperature of between 30 and 60°C and the ratio of volumetric flow rate of total gas at the exit of the reactor to the volumetric flow rate of oxygen introduced into the reactor in stage ($d_1$) is lower than 50.--

This Certificate supersedes Certificate of Correction issued May 3, 1994.

Signed and Sealed this

Twenty-eight Day of March, 1995

Attest:

BRUCE LEHMAN

Attesting Officer     Commissioner of Patents and Trademarks